(12) United States Patent
Das

(10) Patent No.: US 6,426,367 B1
(45) Date of Patent: Jul. 30, 2002

(54) METHODS FOR SELECTIVELY OCCLUDING BLOOD SUPPLIES TO NEOPLASIAS

(75) Inventor: Undurti N. Das, Norwood, MA (US)

(73) Assignee: EFA Sciences LLC, Norwood, MA (US)

( * ) Notice: Subject to any disclaimer, the term of this patent is extended or adjusted under 35 U.S.C. 154(b) by 0 days.

(21) Appl. No.: 09/946,129

(22) Filed: Sep. 4, 2001

Related U.S. Application Data

(63) Continuation-in-part of application No. 09/392,953, filed on Sep. 9, 1999, now abandoned.

(51) Int. Cl.[7] .................. A61K 3/20; A61K 31/225; A61K 9/70
(52) U.S. Cl. .................. 514/560; 424/422; 424/445; 424/449; 514/547
(58) Field of Search .................. 424/422, 445, 424/449, 474, 463; 514/34, 64, 547, 560

(56) References Cited

U.S. PATENT DOCUMENTS

| | | | | |
|---|---|---|---|---|
| 5,246,726 A | * | 9/1993 | Horrobin et al. | 424/648 |
| 5,252,333 A | * | 10/1993 | Horrobin | 424/422 |
| 5,603,959 A | * | 2/1997 | Horrobin et al. | 424/489 |
| 5,763,484 A | * | 6/1998 | Horrobin | 514/560 |
| 5,795,909 A | * | 8/1998 | Shashoua et al. | 514/549 |
| 4,772,590 A | * | 9/1998 | Kawata et al. | 514/34 |
| 5,888,541 A | * | 3/1999 | Horrobin et al. | 424/464 |

FOREIGN PATENT DOCUMENTS

| | | | |
|---|---|---|---|
| EP | 0585057 | * | 2/1994 |
| GB | 2222080 | * | 2/1990 |
| JP | 63 258816 A | * | 2/1989 |
| JP | 08 092129 A | * | 8/1996 |
| WO | 93 05774 A | * | 4/1993 |

OTHER PUBLICATIONS

Hom et al. (1957) "Stabilization of Ethiodol Emulsion For Intravenous Administration," *J. Am. Pharm. Assoc. Sci. Ed.* 46:254257.*
Paxton et al. (1975) "Role of Lymphography in Carcinoma of the Prostate," *Brit. Med. J.* 1:120–122.*
Begin et al. (1985) "Selective Killing of Human Cancer Cells by Polyunsaturated Fatty Acids," *Prostaglandins Leukot. Med.* 19:177–186.*
Begin et al. (1986) "Differential Killing of Human Carcinoma Cells Supplemented With n–3 and n–6 Polyunsaturated Fatty Acids," *J. Natl. Cancer Inst.* 77:1053–1062.*
Begin et al. (1986) "Cytotoxic Effects of Essential Fatty Acids (EFA) in Mixed Cultures of Normal and Malignant Human Cells," *Prog. Lipid Res.* 25:573–576.*
Leary et al. (1987) "Some Effects of Gamma–Linolenic Acid on Cultured HUman Oesophageal Carcinoma Cells," *S. Afr. Med. J.* 62:681–683.*

Seigel et al. (1998) "Cytotoxic Effects of Free Fatty Acids on Ascited Tumor Cells," *J. Natl. Cancer Inst.* 78:271–277.*
Okagaki et al. (1988) "Potentiation of the Antitumor Effect of Aclarubicin on Rat Hepatoma Model By Hepatic Arterially Administered Oily Dosage Forms," *Chem. & Pharm. Bulletin* 3092–3097.*
Das (1990) "Gamma–Linolenic Acid, Arachidonic Acids, and Eicosapentaenoic Acid As Potential Anticancer Drugs," *Nutrition* 6:429–434.*
Das (1991) "Tumoricidal Action of cis–Unsaturated Fatty Acids And Their Relationship to Free Radicals and Lipid Peroxidation," *Cancer Lett.* 56:235–243.
Das (1992) "cis–Unsaturated Fatty Acids As Potential Anti–Mutagenic, Tumoricidal, and Anti–Metastatic Agents," *Asia Pacific J. Pharmacol.* 7:305–327.
Hayashi et al. (1992) "Anticancer Effects of Free Polyunsaturated Fatty Acids In An Oily Lymphographic Agent Following Interhepatic Arterial Administration To A Rabbit Bearing VX–2 Tumor," 52(2) *Cancer Research* 400–405.
Naidu et al. (1992) "Intratumoral Gamma–Linoleic Acid Therapy of Human Gliomas," *Prostaglandins Leukot. Essen. Fatty Acids* 45: 181–184.
Sagar et al. (1992) "Cytotoxic Action of cis–Unsaturated Fatty Acids on Human Cervical Carcinoma (HeLa) Cells: Relationship to Free Radicals and Lipid Peroxidation and Its Modulation By Calmodulin Antagonists," *Cancer Lett.* 63:189–198.
Madhavi et al. (1994) "Effect of n–6 and n–3 Fatty Acids on the Survival of Vincristine Sensitive and Resistant Human Cervical Carcinoma Cells In Vitro," 84 *Cancer Letters* 31–41.
Das (1995) "Tumoricidal Actions of Gamma–Linolenic Acid With Particular Reference To The Therapy of Human Gliomas," 23 *Med. Sci. Research* 507–513.
Das et al. (1995) "Local Application of γ–Linolenic Acid In The Treatment of Human Gliomas," *Cancer Lett.* 94:147–155.

(List continued on next page.)

*Primary Examiner*—Zohreh Fay
*Assistant Examiner*—Brian-Yong Kwon
(74) *Attorney, Agent, or Firm*—Hale and Dorr LLP

(57) ABSTRACT

Disclosed are methods of selectively reducing the blood supply to a neoplastic region, such as a tumor region, thereby selectively causing necrosis of the neoplastic tissue without substantial necrosis of adjoining tissues. In particular, methods are disclosed of selectively reducing the blood supply to a neoplastic region, such as a tumor region, by causing selectively occlusion of blood vessels feeding the neoplastic region. The invention also provides methods of selectively causing anti-angiogenic action in a neoplastic region, such as a tumor region, with the result that new blood vessels are not formed to sustain the neoplasia. The methods employ intra-arterial injection of polyunsaturated fatty acids, preferably in the form of salts, preferably with a lymphographic agent, and optionally with an anti-cancer drug, and/or a cytokine. The invention also provides solutions of PUFAs, or salts of PUFAs, in combination with a lymphographic agent.

18 Claims, No Drawings

OTHER PUBLICATIONS

Visonneau et al. (1997) "Conjugated Linoleic Acid Suppresses the Growth of Human Breast Adenocarcinoma Cells in SCID Mice," *Anticancer Res.* 17:969–73.

Brodie et al. (1999) "Conjugated Linoleic Acid Inhibits Differentiation of Pre– and Post–Confluent 3T3–L1 Preadipocytes But Inhibits Cell Proliferation Only in Preconfluent Cells,"*J. Nutr.* 129:602–6.

Cai et al. (1999) "Inhibition of Angiogenic Factor–and Tumour–Induced Angiogenesis by Gamma Linolenic Acid," 60(1) *Prostaglandins Leukotrienes and Essential Fatty Acids* 21–29.

Das (1999) "Essential Fatty Acids and Their Metabolites and Cancer," *Nutrition* 15:239–241.

* cited by examiner

METHODS FOR SELECTIVELY OCCLUDING BLOOD SUPPLIES TO NEOPLASIAS

RELATED APPLICATIONS

This application is a continuation-in-part of U.S. patent application Ser. No. 09/392,953, filed Sep. 9, 1999, abandoned.

BACKGROUND OF THE INVENTION

1. Field of the Invention

This invention relates to methods for selectively occluding blood vessels which supply neoplastic tissue, including tumors.

2. Description of the Related Art

The polyunsaturated fatty acids (PUFAs) are fatty acids having at least two carbon-to-carbon double bonds in a hydrophobic hydrocarbon chain which typically includes X-Y carbon atoms and terminates in a carboxylic acid group. The PUFAs are classified in accordance with a short hand nomenclature which designates the number of carbon atoms present (chain length), the number of double bonds in the chain and the position of double bonds nearest to the terminal methyl group. The notation "a:b" is used to denote the chain length and number of double bonds, and the notation "n-x" is used to describe the position of the double bond nearest to the methyl group. There are 4 independent families of PUFAs, depending on the parent fatty acid from which they are synthesized. They are:

(1) The "n-3" series derived from alpha-linolenic acid (ALA, 18:3, n-3).

(2) The "n-6" series derived from linoleic acid (LA, 18:2, n-6).

(3) The "n-9" series derived from oleic acid (OA, 18:1, n-9).

(4) The "n-7" series derived from palmitoleic acid (PA, 16:1, n-7).

The parent fatty acids of the n-3 and n-6 series can not be synthesized by the mammals, and hence they are often referred to as "essential fatty acids" (EFAs). Because these compounds are necessary for normal health but cannot be synthesized by the human body, they must be obtained through the diet.

It is believed that both LA and ALA are metabolized by the same set of enzymes. LA is converted to gamma-linolenic acid (GLA, 18:3, n-6) by the action of the enzyme delta-6-desaturase (d-6-d), and GLA is elongated to form di-homo-GLA (DGLA, 20:3, n-6), the precursor of the 1 series of prostaglandins. The reaction catalyzed by d-6-d is the rate limiting step in the metabolism of EFAs. DGLA can also be converted to arachidonic acid (AA, 20:4, n-6)) by the action of the enzyme delta-5-desaturase (d-5-d). AA forms the precursor of 2 series of prostaglandins, thromboxanes and the 4 series leukotrienes. ALA is converted to eicosapentaenoic acid (EPA, 20:5, n-3) by d-6-d and d-5-d. EPA forms the precursor of the 3 series of prostaglandins and the 5 series of leukotrienes. Conjugated linoleic acid (CLA; 18:2) is a group of isomers (mainly 9-cis, 11-trans and 10-trans, 12-cis) of linoleic acid. CLA is the product of rumen fermentation and can be found in the milk and muscle of ruminants (see, e.g., Brodie et al. (1999), *J. Nutr.* 129:602–6; Visonneau et al. (1997), *Anticancer Res.* 17:969–73. LA, GLA, DGLA, AA, ALA, EPA, docosahexaenoic acid (DHA, 22:6, n-3) and CLA are all PUFAs, but only LA and ALA are EFAs.

Under some well defined culture conditions GLA, AA, EPA and DHA showed a marked differential cytotoxic effect against tumor cells with little or no significant action on normal cells (Leary et al. (1987), *S. Afr. Med. J.* 62:681–683; Begin et al, (1985), *Prostaglandins Leukot. Med.* 19:177–186; Das (1999), *Nutrition* 15:239–241; Das (1991), *Cancer Lett.* 56:235–243; Das (1990), *Nutrition* 6:429–434; Seigel et al. (1987), *J. Natl. Cancer Inst.* 78:271–277; Sangeetha and Das (1992), *Cancer Lett.* 63:189–198; Begin et al. (1986), *J. Natl. Cancer Inst.* 77:1053–1062; Das (1992), *Asia Pacific J. Pharmacol.* 7:305–327). In mixed culture experiments, in which both normal and tumor cells were grown together, GLA showed more selective tumoricidal action compared to AA and EPA (Begin et al. (1986), *Prog. Lipid Res.* 25:573–576). In addition, direct intratumoral administration of GLA can regress human gliomas without significant side-effects (Naidu et al. (1992), *Prostaglandins Leukot. Essen. Fatty Acids* 45:181–184; Das et al. (1995), *Cancer Lett.* 94:147–155).

Thus, it is known in the art that certain polyunsaturated fatty acids (PUFAs) have cytotoxic properties towards tumor cells in vitro, and that PUFAs provide the substrates for the generation of lipid peroxidation products which have an inhibitory action on cell proliferation. In addition, tumor cells are known to have low d-6-d activity, which is necessary for the desaturation of LA and ALA to their respective products. Moreover, it has been shown that hepatocarcinogens, diethylnitrosamine (DEN) and 2-acetylamino-fluorine (2-AAF), can suppress the activity of d-6-d and d-5-d resulting in low levels of GLA and AA, EPA and DHA in the tumor cells.

SUMMARY OF THE INVENTION

In one aspect, the present invention provides methods of selectively interrupting the blood supply to a neoplastic region, such as a tumor region, causing necrosis of the neoplastic tissue without substantial necrosis of adjoining tissues. The invention also provides methods of selectively causing anti-angiogenic action in a neoplastic region, such as a tumor region, with the result that new blood vessels and collaterals are not formed to sustain the neoplasia.

In particular, the invention provides methods for selectively reducing blood supply to at least a portion of a neoplastic region, in which (a) a proximal artery which carries blood to at least a portion of said region is located and (b) a therapeutically effective amount of a solution of at least one PUFA is intra-arterially injected into the artery, thereby selectively reducing the blood supply in a period of less than one hour or in a period less than ten minutes. In preferred embodiments, the amount of the solution is sufficient to cause occlusion of the artery in a period of less than one minute. In preferred embodiments, the therapeutically effective amount is between 0.5 mg and 50 gm, most preferably between 250 mg and 5 gm.

In some embodiments of the invention, in addition to the PUFA, a lymphographic agent is intra-arterially injected to visualize the proximal artery and blood supply to the neoplastic region. The lymphographic agent may be combined with the PUFA solution and they may be injected together. The progress of the lymphographic agent through the proximal artery and neoplastic region can be observed to determine when the blood supply is effectively reduced and when injection of the PUFA solution can be stopped. In some embodiments, the lymphographic agent is covalently conjugated to the PUFA.

In some embodiments, the PUFA is an EFA. In certain preferred embodiments, the EFA is selected from linoleic acid, gamma-linolenic acid, arachidonic acid, docosahexaenoic acid, eicosapentaenoic acid, di-homo-gamma-linolenic acid, alpha-linolenic acid, linoleic acid, and conjugated linoleic acid.

In preferred embodiments, the PUFA is administered in the form of free acid or a salt, such as a lithium salt, a sodium salt, magnesium salt, a manganese salt, an iron salt, a copper salt or an iodide salt. In some preferred embodiments, the PUFA is in the form of a fatty acid derivative, such as a glyceride, ester, ether, amide, or phospholipid, or an alkylated, alkoxylated, halogenated, sulfonated, or phosphorylated form of the fatty acid.

In some embodiments of the inventions, the neoplastic tissue is a tumor. In particular, the neoplastic tissue may be a glioma, hepatoma, lung cancer, colon cancer, breast cancer, ovarian cancer, kidney cancer, skin cancer, Kaposi's sarcoma, esophageal cancer, stomach cancer, leukemia, or lymphoma. In other embodiments, the neoplastic tissue may result from a non-cancerous cell proliferative disorder.

In some embodiments of the invention, in addition to the PUFA, a therapeutically effective amount of a compound selected from tumor necrosis factor, anti-cancer drugs, lymphokines, and specific polyclonal or monoclonal antibodies is intra-arterially injected. In preferred embodiments, the lymphokine is alpha interferon or gamma interferon.

In some embodiments, the PUFA is covalently conjugated with a pharmaceutical agent chosen from TNF, alpha-interferon, gamma-interferon, an antibody, vincristine, adriamycin, doxorubicin, cyclophospham-ide, cis-platinum, L-asparaginase, procarbazine, camnptothecin, taxol or busulfan.

In another aspect, the invention provides pharmaceutical compositions of a PUFA, or salt of PUFA, in combination with a lymphographic agent or anti-neoplastic agent.

DETAILED DESCRIPTION

The patent, scientific and medical publications referred to herein establish knowledge that was available to those of ordinary skill in the art at the time the invention was made. The entire disclosures of the issued U.S. patents, published and pending patent applications, and other references cited herein are hereby incorporated by reference.

Definitions

In order to more clearly and concisely describe the subject matter which is the invention, the following definitions are provided for certain terms which are used in the specification and appended claims.

As used herein, the term "neoplastic" means characterized by abnormal tissue that shows partial or complete lack of structural organization and functional coordination with normal tissue, and usually forms a distinct mass which may be either benign or malignant. As used herein, "neoplastic" tissue need not exhibit cellular proliferation that is more rapid than normal tissue (e.g., a tumor which has ceased to grow or which is in remission). Neoplastic tissue need not be cancerous (e.g., uterine fibroids, adenomatous polyps of the intestines, adenomas in the lungs or other organs).

As used herein, a "neoplastic region" means an essentially contiguous region of tissue containing neoplastic tissue. A neoplastic region is the smallest volume of tissue that includes the contiguous neoplastic tissue, but may also include normal tissue. Contiguous neoplastic tissues are neoplastic tissues separated by distances of less than one centimeter, and do not include distant metastases (which define separate neoplastic regions). Although not all neoplastic regions are tumors, the terms "neoplastic region" and "tumor" will often be used interchangeably herein, and the term "tumor-feeding vessel" should be understood to include an artery feeding any type of neoplastic region.

As used herein, the term "polyunsaturated fatty acid" and the abbreviation "PUFA" mean any acid derived from fats by hydrolysis, or any long-chain (at least 12 carbons) organic acid, having at least two carbon-to-carbon double bonds. Examples of PUFAs include but are not limited to linoleic acid, linolenic acid and arachidonic acid.

As used herein, the term "PUFA salt" means an ionic association, in solid or in solution, of a anionic form of a PUFA with a cation of a small organic group (e.g., ammonium) or a small inorganic group (e.g., an alkali metal). Preferred salts are those between a PUFA and an alkali metal (e.g., lithium, sodium, potassium), an alkali earth metal (e.g., magnesium, calcium) or a multivalent transition metal (e.g., manganese, iron, copper, aluminum, zinc, chromium, cobalt, nickel).

As used herein the term "lymphographic agent" means any of the class of compounds which are used, or may be used, to visualize lymphatics and lymph nodes, as well as veins and arteries, following an intravenous or intra-arterial injection. Lymphographic agents are typically vegetable oils (e.g., poppy seed oil) which are iodized (e.g., approximately 30–45% by weight), and which may be further derivatized (e.g., ethyl esterification). Examples include the iodized fatty acids of poppy seed oil (commercially available as LIPIODOL ULTRA FLUIDE® from Laboratoire Guerbet, Paris., France), the ethiodized fatty acids of poppy seed oil (commercially available as ETHIODOL® from Savage Laboratories, Melville, N.Y.) and iophendylate (PANTOPAQUE® from Kodak). See, Hom et al. (1957), *J. Am. Pharm. Assoc. Sci. Ed.* 46:254; Paxton et al. (1975), *Brit. Med. J.* 1:120. As used herein, the term "lymphographic agent" means any agent which is useful for non-invasively visualizing blood vessels including, without limitation, radiography, CAT scans, MRI scans, ultrasound imaging, and the like.

As used herein, the term "angiogram" means any method of noninvasively visualizing a blood vessel or lymphatic including, without limitation, radiography, CAT scans, MRI scans, ultrasound imaging, and the like.

As used herein, the term "proximal" is a relative term which describes the location of an artery with respect to a neoplastic region and a site of intra-arterial injection of a PUFA salt of the invention. An artery is proximal to a neoplastic region if it is upstream of the neoplastic region with respect to blood flow and downstream (or distal) of the site of injection with respect to blood flow. A proximal artery should also be physically close to the neoplastic region such that a substantial portion (e.g., at least 10%, preferably 25%, most preferably greater than 50%) of the volume of a solution injected into the artery would normally pass into arteries, arterioles and capillary beds within the neoplastic region.

General Considerations

The present invention is dependent, in part, upon the discovery of the novel and highly beneficial action of PUFAs, and especially certain PUFA salts, to induce the selective occlusion of blood vessels feeding neoplastic regions, including tumors. This effect is particularly observed when the PUFA is administered in combination with a lymphographic agent comprising iodized fatty acids.

Without being bound to any particular theory of the invention, it is believed that the selective occlusion of the tumor-feeding vessels is not due to embolism or other forms of physical blockage. This conclusion follows from observations in several patients that normal blood vessels, which were sometimes smaller in diameter than tumor-feeding vessels, which were located proximal to the tumor-feeding vessels, and which were closer to the tip of the catheter and the site of injection, were not occluded. If the occlusion were due to embolization, all blood vessels, especially those that were smaller in diameter compared to the tumor-feeding vessels, would be expected to be occluded first. Because the site of injection of the PUFA, as determined by angiographic imaging of the tip of the catheter in several patients, was slightly upstream from the origin of the main tumor-feeding vessels, it is evident that the occlusion of the tumor-feeding vessels is not due to direct injection of the PUFA only into those vessels. Rather, the ability of PUFA to selectively occlude the tumor-feeding vessels but not normal arterial vessels was seen in several patients.

Moreover, in several other patients, a PUFA was injected into normal arteries including the celiac, subclavian and popliteal arteries. During the course of these procedures, no spasms or occlusions (even temporary) of these blood vessels were observed. On the other hand, the PUFA occluded all types of tumor-feeding vessels, irrespective of their size, almost instantaneously. Without being bound to any particular theory of the invention, this rapid action of the PUFA suggests that an intense vasospasm was induced (directly or indirectly) in the tumor-feeding vessels but not in the normal blood vessels and that, following such a vasospasm, thrombosis may have led to permanent occlusion of the blood vessel.

Finally, without being bound to any particular theory of the invention, it is believed that there is an interaction between the PUFA and lymphographic agents of the invention which may account for the effectiveness of the treatment. Thus, lymphographic agents comprising iodized fatty acids, and particularly the iodized fatty acids of vegetable oils, are believed to synergistically interact with the PUFAs to produce a therapeutic effect which is qualitatively different than the effect of either the PUFA or the lymphographic agent alone.

There are several advantages of PUFA treatments of the invention. As shown below, a single injection (or at most two or three injections at separate times, if the neoplastic region is large) is adequate to produce almost permanent occlusion of the tumor-feeding vessels. The PUFAs and their salts are non-antigenic, are known to be relatively safe in the dosages employed, and are stable. The dosage of PUFA needed to occlude the tumor-feeding vessels in a given patient is self-evident during administration: As the PUFA solution is being injected, and as the tumor-feeding vessels are being occluded, resistance to further injection will be felt, at which point the injection can be stopped.

The invention in one aspect provides methods of inhibiting blood supply to a neoplastic region, comprising the steps of (a) locating an artery which carries major blood supply to the neoplastic region and which is proximal to the neoplastic region; and (b) intra-arterially injecting into the located artery a solution of at least one PUFA chosen from LA, GLA, DGLA, AA, ALA, EPA, DHA and CLA. In preferred embodiments, the PUFA is administered in combination with a lymphographic agent.

The invention in another aspect provides methods for treating neoplasias and for facilitating the visualization of remission of a neoplasia which is responsive to treatment, comprising the steps of (a) locating an artery proximal to the neoplastic region which carries a major portion of blood supply to the neoplastic region and which is adjacent to the neoplastic region; (b) obtaining an initial radiographic image of the region; (c) injecting into the artery a mixture of (i) a lymphographic agent, and (ii) a solution of at least one PUFA chosen from LA, GLA, DGLA, AA, ALA, EPA, DHA and CLA; and (d) obtaining second and, optionally, subsequent radiographic images of the neoplastic region after predetermined lapses of time; and comparing the initial radiographic images with the second and/or subsequent radiographic images to assess the extent of remission of the neoplasia.

The invention in another aspect provides methods of causing necrosis in a neoplastic region (e.g., a cancerous tumor) by inhibiting blood supply to the neoplastic region, comprising the steps of (a) locating an artery proximal to the neoplastic region which carries major blood supply to the neoplastic region; (b) injecting into the located artery a mixture of (i) a lymphographic agent, and (ii) a solution of at least one PUFA chosen from LA, GLA, DGLA, AA, ALA, EPA, DHA and CLA; (c) waiting for a predetermined time period and assessing a degree of necrosis in the neoplastic region; and (d) repeating the treatment if necessary to increase the necrosis.

In yet another aspect, the invention provides methods of treating mammalian cell proliferative disorders using a solution of a PUFA, or combinations of PUFAs, administered intra-arterially. The methods are as described above with respect to neoplastic regions.

In each of the foregoing embodiments, the PUFA is preferably in the form of a salt, most preferably in the form of a lithium salt, and is preferably administered in combination with a lymphographic agent. The lymphographic agent is preferably an iodized fatty acid derived from a vegetable oil.

Although the invention is described primarily as it relates to humans, it is envisaged that the methods of the invention are equally applicable to other mammals, including large domesticated mammals (e.g., race horses, breeding cattle) and smaller domesticated animals (e.g., house pets).

Choice of PUFA

The present invention employs PUFAs, preferably in the form of salts, to selectively occlude arteries which provide blood supply to regions of neoplastic tissue. Preferred PUFAs include, but are not limited to, GLA, AA, DHA, EPA, DGLA, ALA, LA and CLA. Other preferred PUFAs include derivatives of the aforementioned PUFAs, including glycerides, esters, ethers, amides, or phospholipids, or alkylated, alkoxylated, halogenated, sulfonated, or phosphorylated forms of the fatty acid. In most preferred embodiments, the PUFA is GLA, AA or DHA.

The PUFA is preferably administered in the form of a salt solution. Suitable salts include salts of a PUFA with a cation of a small organic group (e.g., ammonium) or a small inorganic group (e.g., an alkali metal or alkali earth metal). Preferred referred salts are those between a PUFA and an alkali metal (e.g., lithium, sodium, potassium), an alkali earth metal (e.g., magnesium, calcium) or a multivalent metal (e.g., manganese, iron, copper, aluminum, zinc, chromium, cobalt, nickel). Most preferred are salts of lithium, sodium, magnesium, manganese, iron, copper, and iodides. Combinations of salts may also be employed.

When the PUFAs or PUFA salts are administered in combination with an oily lymphographic agent or other agents, the solution may be formed into an emulsion.

Lymphographic Agents

In order to visualize lymphatic vessels, lymph nodes, arteries and veins, lymphographic agents are frequently employed. In the context of the present invention, these agents may aid in both the placement of a syringe or catheter in a proximal artery for intra-arterial injection of a PUFA solution, and may also aid in the visualization of the resulting selective occlusion of tumor-feeding vessels. In addition, such agents may be used in follow-up angiograms to determine whether occlusion has been successful or complete, and to determine whether additional treatments may be necessary. Finally, it is believed that such agents have a synergistic or potentiating effect in combination with the PUFA solutions of the invention, and thereby serve as additional or ancillary active ingredients in the treatments of the invention.

The lymphographic agents can be any of the class of compounds, recognized by those of skill in the art of diagnostic imaging, which are used, or which may be used, to visualize lymphatics and lymph nodes, as well as veins and arteries, by radiography following an intra-lumenal injection. Lymphographic agents are typically vegetable oils (e.g., poppy seed oil) which are iodized (e.g., approximately 30–45% by weight), and which may be further derivatized (e.g., ethyl esterification). Examples include the iodized fatty acids of poppy seed oil (commercially available as LIPIODOL ULTRA FLUIDE® from Laboratoire Guerbet, Paris, France), the ethiodized fatty acids of poppy seed oil (commercially available as ETHIODOL® from Savage Laboratories, Melville, N.Y.) and iophendylate (PANTOPAQUE® from Kodak). See, Hom et al. (1957), *J. Am. Pharm. Assoc. Sci. Ed.* 46:254; Paxton et al. (1975), *Brit. Med. J.* 1:120.

The lymphographic agents of the invention may be mixed with the PUFA solutions described above, either to form a new solution or to form an emulsion, or they may be chemically conjugated to the PUFAs of the invention via standard chemistries. Preferably the lymphographic agent is an iodized lymphographic oil, such as an iodized poppy seed oil. Preferably the PUFA solution is mixed with such a lymphographic agent in a ratio of at least about 2:1, or about 1:1, or about 1:1.5, or about 1:2, or about 1:3 (volume/volume). Most preferably the ratio is between 1:1.5 and 1:3 (volume/volume). The preferred lymphographic agent is LIPIODOL ULTRA FLUIDE® (Laboratoire Guerbet, Paris, France). This lymphographic agent may be safely administered to a typical patient in an amount of about 10 mL/m$^2$, but the attending physician should consider all relevant medical factors in determining the appropriate dosage for any specific patient.

Thus, in another aspect, the invention provides pharmaceutical compositions comprising a PUFA, or a PUFA salt, and a lymphographic agent in solution, or in an emulsion. The PUFA and lymphographic agent may be separate chemical moieties combined in the solution or emulsion, or they may be covalently conjugated. The preferred lymphographic agents and ratios for such a product are as disclosed above. Preferably the final concentration of the PUFA in such a product is at least 5%, preferably at least 20%, and most preferably about 25–50%.

Methods of Administration

The PUFA solutions of the present invention are preferably administered intra-arterially to an artery which is proximal to the neoplastic region to be treated. The approximate location of the neoplastic region must first be identified by any of the methods known in the art. For example, X-rays, Computerized Axial Tomography (CAT) scans, Magnetic Resonance Imaging (MRI) scans, palpation or direct visual inspection may be used to identify a neoplastic region. Such methods may optionally employ contrast agents, including lymphographic agents or agents specifically targeted to neoplastic tissues (e.g., radioisotope-labeled antibodies against tumor-associated antigens). Once the neoplastic region is identified, an artery which feeds the region (i.e., which is upstream with respect to blood flow to the region) is identified. The intra-arterial injection site is preferably chosen to be close or proximal to the neoplastic region to increase the portion of the dosage which reaches that region, but is also preferably chosen sufficiently far upstream from that region such that all or most of the neoplastic region receives a portion of the injected dosage.

Thus, as one progresses along an artery which feeds a neoplastic region, the artery will branch into smaller and smaller arteries and finally arterioles. At some distant point upstream from the neoplastic region, the artery will feed not only the neoplastic region but also large regions of normal tissue. As the chosen injection site is moved along the artery toward the neoplastic region, the percentage of blood carried by the artery which feeds normal tissue will decrease. By proceeding along the artery toward the neoplastic region, therefore, one can increase the portion of the dosage which reaches the neoplastic region. However, as the injection site proceeds along the artery toward the neoplastic region, one may also bypass branches of the artery which feed the neoplastic region and, therefore, fail to cause occlusion of arteries supplying a part of the neoplastic region. One of ordinary skill in the art may balance these considerations, as well as other considerations (e.g., accessibility of an artery for catheterization), in choosing a site for injection. Thus, the term "proximal" is a relative term which describes the location of an artery with respect to a neoplastic region and a site of intra-arterial injection of a PUFA of the invention. Preferably, a proximal artery should also be physically close to the neoplastic region such that a substantial portion (e.g., at least 10%, preferably 25%, and most preferably greater than 50%) of the volume of a solution injected into the artery would normally pass into arteries, arterioles and capillary beds within the neoplastic region. Thus, the hepatic artery might be considered proximal to a neoplastic region in the liver, but the descending aorta would not.

In order to administer a PUFA solution to a proximal artery, the artery is identified as described above, the site of injection is chosen, and the PUFA solution is administered by injection through a syringe or catheter as appropriate to the location. As necessary, the syringe or catheter may be guided to the site of injection by radiological guidance (e.g., X-rays), CAT guidance, MRI guidance, endoscopic guidance, or stereotaxic guidance. In the case of a catheter, the catheter can be inserted into the body at a site quite distant from the proximal artery, and then be guided to the proximal artery. For example, the femoral, brachial and carotid arteries may provide convenient entry points for a catheter which is then routed to a proximal artery elsewhere in the body. In addition, contrast agents may be added to the injected solution to aid in placement of the syringe or catheter, or to aid in visualization of the occlusion of the tumor-feeding vessels.

Appropriate dosages of the PUFA solutions of the invention will depend primarily on the diameter of the proximal artery at the site of injection and the number and size of the arteries and/or arterioles branching therefrom. Preferred dosages range from approximately 0.5 mg for the smallest proximal arteries to 50 gm for very large proximal arteries feeding large neoplastic regions. More typically, dosages of approximately 250 mg to 5 gm are preferred and, as shown in the examples below, dosages of 500 mg to 750 mg are effective for several different types of tumors. However, in most preferred embodiments of the methods of the invention, the PUFA solution is administered in combination with a lymphographic agent, the administration is observed by angiogram, and administration continues until the tumor-feeding vessels are at least partially occluded as indicated by the angiogram. Alternatively or additionally, administration may be continued until a significant increase in resistance to the injection develops, indicating the tumor-feeding vessels distal to the site of injection have been at least partially occluded.

Other Agents

The PUFA solutions of the invention may be administered alone, or in combination with other pharmaceutical agents known in the art for the treatment of neoplasias. Thus, for example, the PUFA solutions may be co-administered with known anti-cancer drugs, including vincristine, adriamycin, doxorubicin, cyclophosphamide, cis-platinum, L-asparaginase, procarbazine, camptothecin, taxol and busulfan. Alternatively, the PUFA solutions may be co-administered with known lymphokines such as tumor necrosis factor (TNF) and/or an interferon (e.g., alpha interferon or gamma interferon) or specific polyclonal or monoclonal antibodies.

Administration of these agents in combination with a PUFA solution, or a PUFA and lymphographic agent solution, may also show a synergistic or potentiating effect.

Thus, in another aspect, the invention provides pharmaceutical compositions comprising a PUFA, or a PUFA salt, and a pharmaceutical agent known in the art for the treatment of neoplasias, either in solution, or in an emulsion. The PUFA and other pharmaceutical agent may be separate chemical moieties combined in the solution or emulsion, or they may be covalently conjugated. The preferred pharmaceutical agents are as disclosed above. Preferably the final concentration of the PUFA in such a product is at least 5%, preferably at least 15%, and most preferably at least 25%. The product may contain substantially more PUFA, up to 100% without any significant side-effects.

The following examples illustrate some preferred modes of practicing the present invention, but are not intended to limit the scope of the claimed invention. Alternative materials and methods may be utilized to obtain similar results.

EXAMPLES

Patients

Studies were conducted in 5 human patients with stage 4 neoplastic disease. Two of the patients had primary hepatoma (patients 1 and 2), two had giant cell tumor of the bone (patients 3 and 4) and one had renal cell carcinoma (patient 5).

Materials

The lithium salt of GLA was obtained from Scotia Pharmaceuticals, U.K. The PUFA salt was dissolved in sterile saline, sterile phosphate buffered saline (PBS, pH 7.4) or dilute ethanol in saline (final concentration <0.02% ethanol). The final concentration of PUFA in these solutions was approximately 25%. The PUFA solution was mixed with an iodized lymphographic oil (LIPIODOL ULTRA FLUIDE®, Laboratoire Guerbet, Paris, France), in a ratio of between 1:1.5 and 1:3 (volume/volume). In some cases, the PUFA was modified by covalent conjugation (e.g., amide bond) to the iodized lymphographic oil. In other cases the PUFA salt was unmodified, and was diluted directly into the lymphographic agent without conjugation. The PUFA and lymphographic oil mixture was prepared under sterile conditions immediately prior to use.

Methods of Administration

Patients were admitted into the hospital for the study. A proximal artery suppling a major portion of the blood supply to the tumor was identified. Catheterization of the major artery from which the proximal artery arises was performed under local anaesthesia. In patients 1 and 2 (with hepatomas), the tip of the catheter was positioned in the right hepatic artery via the right femoral artery. In patient 3 (with giant cell tumor of the right lower end of the femur), the tip of the catheter was positioned in the right femoral/popliteal artery. In patient 4 (with giant cell tumor of the left scapula), the tip of the catheter was positioned in the left subdlavian/axillary arteries. In patient 5 (with left kidney tumor), the tip of the catheter was positioned in the left renal artery. Conjugated PUFA salt was prepared fresh, just prior to injection. Radiographic and CT scan examinations were performed immediately after the injection and at periodic intervals in all the five patients.

In order to determine how the arterial supply to the tumor tissue was influenced by the injection of PUFA salt, angiography was performed and recorded during and immediately after the procedure, and at periodic intervals thereafter.

Patients 1 and 2 with hepatoma were administered total doses of 1.6 gm and 0.75 gm respectively (the dose refers to the amount of Li-GLA) of PUFA salt into the right hepatic artery through the right femoral route. Patient 3, with giant cell tumor of the lower end of the right femur, underwent right femoral artery catheterization and the tip of the catheter was positioned in the popliteal artery to deliver 500 mg of PUFA salt. Patient 4, who had giant cell tumor of the left scapula, received PUFA salt by selective cannulation of the left subdlavian artery, through the femoral route, from which the tumor-feeding vessel was arising and was given 660 mg of PUFA salt. Patient 5, with renal tumor, received 750 mg of PUFA salt through the right femoral route into the left renal artery from which the tumor-feeding vessels were arising. In all the patients, the administration of PUFA salt was done as swiftly as possible. During the administration of PUFA salt, the vital signs of each patient were monitored.

Summary Results

All 5 patients tolerated the treatment well and no significant side-effects due to the therapy were noted. The only side-effect was a complaint of a mild feeling of warmth followed by pain at the site of the tumor during and immediately after the injection of the PUFA salt. This was presumably due to the perfusion of the tumor with the PUFA salt, and ischaemia resulting from occlusion of the tumor-feeding vessels. In general, the pain was not severe and was ameliorated by the administration of non-steroidal anti-inflammatory drugs (NSAIDs), such as ibuprofen or buscopan. All the biochemical tests performed after the administration of the PUFA salt were found to be normal.

The most significant and surprising observation of these studies was the total occlusion of the tumor-feeding vessels following PUFA salt injection. This was a a consistent observation in all the 5 patients. This selective occlusion of the tumor-feeding vessels was seen during the course of injecting the PUFA salt in the patients with giant cell tumors of the bone and the patient with renal cell carcinoma. In the case of the patients with hepatomas, the occlusion of the tumor-feeding vessels was noticed over a period of time. In patient 1 the occlusion of the tumor-feeding vessels was observed 10 days after the first injection of PUFA salt, and six days after a second injection, but presumably occurred during or shortly after the second injection. No occlusion was seen in the normal vasculature feeding non-neoplastic tissues. The time lag for the occlusion of the tumor-feeding vessels observed in patient 1 with hepatoma suggests that the occlusion of the tumor-feeding vessels is not due to an embolization process. Moreover, normal blood vessels, which were much smaller in diameter compared to the tumor-feeding vessels, were not occluded when exposed to PUFA salt, further suggesting that embolization was not the mechanism. On the other hand, in patient 2, also with hepatoma, the occlusion of the tumor-feeding vessels was seen essentially simultaneously with the injection of the PUFA salt. The remarkably selective occlusion of only the tumor-feeding vessels was clear from pre- and post-injection angiograms of patient 5 with the renal cancer. These angiograms showed that the three main tumor-feeding vessels arising from the main renal artery were completely occluded whereas the fourth and the fifth branches arising from the main stem of the left renal artery, which were feeding the normal lower pole of the kidney, were not occluded. This was despite the fact that all the five vessels were arising from the same renal artery, downstream from the point of injection. If the occlusion of the vessels were the result of embolization, it is expected that the lower most and narrower branches should have been occluded first and later the other vessels.

The pre and post-injection angiograms of all the 5 patients indicated that PUFA salt can selectively occlude tumor-feeding vessels. In order to know the duration of this selective occlusion of the tumor-feeding vessels, angiograms were repeated at periodic intervals. It was noted that even 28 days after PUFA salt injection, no tumor-feeding vessels could be seen in patient 1 with hepatoma. In the patient with giant cell tumor of the lower end of the right femur (patient 3), a repeat angiogram performed after 10 days following PUFA salt injection also did not show any tumor-feeding vessels. Radiographs of the right knee of this patient taken 10 days after the injection clearly showed the presence of the contrast material, which is due to the presence of conjugated PUFA salt in the tumor tissue. In the patient with giant cell tumor of the left scapula (patient 4), a follow up angiogram performed seven and a half years after the injection of PUFA salt clearly showed that the original tumor-feeding vessel was still occluded. A plain radiograph of the left scapula showed extensive sclerosis of the tumor, and attempts to do a fine needle aspiration biopsy of the healed mass were unsuccessful due to its hard, bony nature.

Detailed Results

Patient 1. Patient 1 was a 45 year old male. The patient was diagnosed to have hepatoma of the right lobe of the liver confirmed by fine needle aspiration biopsy (FNAB). The patient was considered unsuitable for surgery, radiotherapy and chemotherapy due to poor general condition and large size of the tumor. The patient had lost more than 25 kgs prior to confirmation of the diagnosis. Prior to the treatment, a pronounced "tumor blush" was observed in angiograms. In a first treatment, 1.1 gm of PUFA salt was administered. More than 50% of the tumor-feeding vessels were occluded following the first injection, and a significant amount of resistance was noted while injecting the first dose of PUFA salt. A repeat angiogram done 4 days after the first dose of the PUFA salt showed that the tumor blush was much reduced. At that time, an additional dose of 0.5 gm of PUFA was administered. A third angiogram performed 1 week after the second dose of PUFA salt (and the 11th day after the first dose) showed almost complete occlusion of the tumor-feeding vessels. No such occlusion was seen in the normal vasculature feeding non-neoplastic tissues. A >50% reduction in the size of the hepatoma in patient 1 was seen one month after the first PUFA salt injection. The decrease in the size of hepatoma was associated with an increase in the radiographic density of the contrast agent. This suggests that, as the size of the tumor was decreasing, there was a concomitant increase in the density of the contrast agent (to which the PUFA salt was conjugated) in the remaining portion of the tumor. The patient felt well for 6 months following the injection, gained >10 kgs in weight, and was a symptomatic. Unfortunately, the patient died in a traffic accident.

Patient 2. Patient 2 was a 50 year old male. The patient was diagnosed to have hepatoma of the right lobe of the liver confirmed by FNAB, and was considered to be high risk for surgery, and unlikely to respond to radiotherapy and/or chemotherapy. During the course of injecting the PUFA salt, significant resistance was felt and therefore only 750 mg of PUFA salt was administered into the right hepatic artery. An angiogram recorded immediately after the injection showed complete occlusion of the tumor-feeding vessels. The patient experienced a mild to moderate degree of pain in the hepatic region during and after the injection, which subsided after administering NSAIDs (ibuprofen). The pain subsided after 24 to 48 hours. This patient developed peritonitis 1 week after the PUFA administration. Subsequent investigations revealed that the patient had developed a perforated duodenal ulcer, which was responsible for the peritonitis but presumably unrelated to the PUFA injection. The patient died on the 10th day due to complications of the perforated duodenal ulcer.

Patient 3. Patient 3 was a 24 year old male. The patient was diagnosed to have giant cell tumor (osteoclastoma) involving the medial condyle of the right femur. The diagnosis was confirmed by biopsy. The patient refused the recommended surgical amputation above the right knee, and opted to try a PUFA injection. A total dose of 500 mg of PUFA salt was delivered into the femoral/popliteal artery. Complete occlusion of the tumor-feeding vessels was noted immediately after the injection. The patient complained of pain in the right knee area and was given NSAIDs. A repeat angiogram done 10 days after the injection of PUFA salt showed that the occluded tumor-feeding vessels remained closed. The patient appeared for a follow-up 2 months after the injection, at which time he reported that he was better except for mild pain in the region of the tumor. The patient was subsequently lost for follow up visits.

Patient 4. Patient 4 was a 30 year old male. The patient was diagnosed to have giant cell tumor of the left scapula, confirmed by biopsy. The patient refused the recommended surgical removal of the left upper limb and opted to try a PUFA injection. The patient received 660 mg of PUFA salt through selective catheterization of the left subclavian artery. During the course of the injection, significant resistance was felt and the injection was stopped after delivering 660 mg of PUFA salt. Complete occlusion of the tumor-feeding vessels was seen immediately after the administration of PUFA salt. This patient was discharged from the hospital after 24 hours of observation. The patient felt better and was able to do use his left arm normally, without any pain or limitation of movement. Seven and a half years after the PUFA salt injection, an angiogram showed that the tumor-feeding vessels were still occluded and that the tumor mass was completely calcified. Attempts at FNAB were not successful due to hard nature of the healed mass.

Patient 5. Patient 5 was a 79 year old male. This patient was diagnosed to have right renal cell carcinoma. By the time it was diagnosed, the disease was well advanced, with secondary tumors in the liver, peritoneum and right pleural effusion. The patient had lost about 10 kgs of weight and was considered a high risk for surgery. In a first treatment, 750 mg of PUFA salt was delivered into the right renal artery via the right femoral route. Complete occlusion of the tumor-feeding arteries was noted without any occlusion of the normal arteries which were feeding the normal lower pole of the right kidney. The patient experienced mild to moderate pain at the site of tumor (right lumbar area). The pain subsided after administering NSAIDs. The patient complained of pain in the right knee area and was given NSAIDs (buscopan by injection and oral ibuprofen). The patient was sent home 48 hours after PUFA salt injection. The patient survived for 3 months, and then died due to extensive metastasis in the liver and lungs.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize, or be able to ascertain using no more than routine experimentation, many equivalents to the specific embodiments of the invention described specifically herein. Such equivalents are intended to be encompassed in the scope of the appended claims.

What is claimed is:

1. A method of selectively reducing blood supply to at least a portion of a neoplastic region comprising:

locating a proximal artery which carries blood to at least a portion of said region; and administering a therapeutically effective amount of a solution of at least one polyunsaturated fatty acid by intra-arterial injection into said artery, whereby said blood supply is selectively reduced without said polyunsaturated fatty acid form of an embolism or other form of physical blockage.

2. A method as in claim 1 further comprising administering a lymphographic agent by intra-arterial injection into said artery, whereby said artery and said blood supply can be visualized by angiogram.

3. A method as in claim 2 wherein said lymphographic agent is combined with said polyunsaturated fatty acid in said solution.

4. A method as in claim 2 wherein said lymphographic agent is conjugated to said polyunsaturated fatty acid.

5. A method as in claim 2 further comprising the steps of:

observing the passage of said lymphographic agent into said proximal artery and said neoplastic region by angiogram;

determining when said blood supply has been reduced by at least partial occlusion of blood vessels in said neoplastic region; and terminating said injection.

6. A method as in claim 5 wherein said therapeutically effective amount is an amount effective to cause at least partial occlusion of blood vessels in said neoplastic region as determined by said angiogram.

7. A method as in any one of claims 1–6 wherein said therapeutically effective amount is sufficient to cause occlusion of said artery in a period of less than one hour.

8. A method as in claim 7 wherein said therapeutically effective amount is sufficient to cause occlusion of said artery in a period of less than ten minutes.

9. A method as in claim 7 wherein said therapeutically effective amount is sufficient to cause occlusion of said artery during perfusion of said artery with said solution.

10. A method as in claim 7 herein said therapeutically effective amount is between 0.5 mg and 50 gm.

11. A method as in claim 7 wherein said therapeutically effective amount is between 250 mg and 5 gm.

12. A method as in any one of claims 1–6 wherein said polyunsaturated fatty acid is an essential fatty acid.

13. A method as in claim 12 wherein said essential fatty acid is selected from the group consisting of gamma-linolenic acid, arachidonic acid, docosahexaenoic acid, eicosapentaenoic acid, di-homo-gamma-linolenic acid, alpha-linolenic acid, linoleic acid, and conjugated linoleic acid.

14. A method as in any one of claims 1–6 wherein said polyunsaturated fatty acid is administered in the form of a salt selected from the group consisting of a lithium salt, a sodium salt, a potassium salt, a magnesium salt, a calcium salt, a manganese salt, an iron salt, a copper salt, an aluminum salt, a zinc salt, a chromium salt, a cobalt salt, a nickel salt and an iodide.

15. A method as in any one of claims 1–6 wherein said polyunsaturated fatty acid is in the form of a fatty acid derivative selected from the group consisting of glycerides, esters, free acids, amides, phospholipids and salts.

16. A method as in any one of claims 1–6 further comprising injecting, together with or separately from the polyunsaturated fatty acid, a therapeutically effective amount of a compound selected from the group consisting of tumor necrosis factor, an anti-cancer drug, a lymphokine, and specific polyclonal or monoclonal antibodies.

17. A method as in claim 16 wherein said lymphokine is selected from the group consisting of alpha interferon and gamma interferon.

18. A method as in any one of claims 1–6 wherein said polyunsaturated fatty acid is covalently conjugated to a pharmaceutical agent chosen from the group consisting of vincristine, adriamycin, doxorubicin, cyclophosphamide, cis-platinum, L-asparaginase, procarbazine, camptothecin, taxol and busulfan.

* * * * *